US006925391B1

United States Patent
Pesce et al.

(10) Patent No.: US 6,925,391 B1
(45) Date of Patent: Aug. 2, 2005

(54) METHODS AND APPARATUS FOR DETECTING ARTIFACTUAL OUTPUT FROM A CHEMICAL ANALYZER

(75) Inventors: Amadeo J. Pesce, Cincinnati, OH (US); Marios M. Polycarpou, Cincinnati, OH (US); Zhong Wang, Cincinnati, OH (US); Goce Dimeski, Queensland (AU); Peter Hickman, Queensland (AU)

(73) Assignees: University of Cincinnati, Cincinnati, OH (US); The State of Queensland, Brisbane (AU)

( * ) Notice: Subject to any disclaimer, the term of this patent is extended or adjusted under 35 U.S.C. 154(b) by 146 days.

(21) Appl. No.: 10/130,897

(22) PCT Filed: Nov. 14, 2000

(86) PCT No.: PCT/US00/31269

§ 371 (c)(1),
(2), (4) Date: Aug. 16, 2002

(87) PCT Pub. No.: WO01/38881

PCT Pub. Date: May 31, 2001

Related U.S. Application Data

(60) Provisional application No. 60/166,983, filed on Nov. 23, 1999.

(51) Int. Cl.[7] .............................................. G06F 15/00

(52) U.S. Cl. ...................................................... 702/21

(58) Field of Search ............................ 702/21, 63, 183, 702/19; 600/300, 544, 584; 607/32; 436/518, 174, 43; 435/4, 6, 254; 606/182; 370/230; 707/6, 1; 382/128, 181, 190; 434/262; 705/2, 19, 9, 3; 704/9; 703/11; 700/7, 18, 19, 83; 706/21

(56) References Cited

U.S. PATENT DOCUMENTS

| 4,708,940 A | | 11/1987 | Yoshida et al. |
| 5,374,395 A | | 12/1994 | Robinson et al. |
| 5,642,936 A | * | 7/1997 | Evans .......................... 600/300 |
| 5,713,938 A | * | 2/1998 | Chiang et al. ................. 607/32 |
| 5,937,364 A | | 8/1999 | Westgard et al. |
| 6,282,305 B1 | * | 8/2001 | Huo et al. ................... 382/128 |
| 6,556,951 B1 | * | 4/2003 | Deleo et al. ................. 702/183 |

FOREIGN PATENT DOCUMENTS

| EP | 0 316 861 A2 | 5/1989 |
| EP | 0 908 724 A1 | 4/1999 |

OTHER PUBLICATIONS

Written Opinion from corresponding PCT application (Application No. PCT/US00/31269), Apr. 16, 2004.

Kelman, A., et al., Computer Programs in Biomedicine, *Parameter optimisation in clinical pharmacokinetics*, vol. 14, pp. 239–248, 1982.

(Continued)

*Primary Examiner*—Michael Nghiem
*Assistant Examiner*—Tung Lau
(74) *Attorney, Agent, or Firm*—Dinsmore & Shohl LLP

(57) ABSTRACT

A method and apparatus for examining data from a chemical analyzer for artifactual results. A set of rules are established to identify artifactual results based upon experience with the analyzer. Moreover, each rule can be associated with a sample collection or testing problem which potentially caused the artifactual result. Using these rules, output data from the analyzer can be tested to see if any of the rules are satisfied. If a rule is satisfied, then an artifactual result can be indicated, as well as the potential cause of the artifactual result. An output file can be created which indicates the artifactual data samples and the potential artifactual causes. Preferably, the rules are provided in a user-modifiable data file, so that the rules may be modified based upon additional experience.

12 Claims, 8 Drawing Sheets

OTHER PUBLICATIONS

Biondo, Samual J., Fundamentals of Expert System Technology, Table of Contents, Chapters V–VII, IX, X, 1990.

Bielawski, Larry et al., *Expert System Development: Building PC–Based Applications*, QED Information Science, Inc., pp. vii–xiii, 1–160, 1988.

Solfberg, Helge Erik, *RefVal: A Program implementing the recommendations of the International Federation of Clinical Chemistry on the statistical treatment of reference values*—EIX 96–11 EIX96113009592 NDN–017–0244–0108–4, Computer Methods and Programs in Biomedicine, vol. 48, No. 3, pp. 247–256, Dec. 1995.

Fuentes–Arderiu, X. et al., *Evaluation of the VALAB expert system*—MED 98–02 98013488 NDN–194–0065–8711–0, European Journal Clinical Chemistry Clinical Biochemical, vol. 35, No. 9, pp. 711–4, Sep. 1997.

Place, J.F. et al., *International Federation of Clinical Chemistry Use of artifical intelligence in analytical systems for the clinical laboratory—IFCC Committee on Analytical Systems*—MED 95–06 95196302 NDN–193–0082–9727–5, Clinical Chim. Acta., vol. 231, No. 2, pp. S5–34, Dec. 16, 1994.

Alwan, L.C. et al., *Time series modeling for quality control in clinical chemistry*—MED 88–10 88270667 NDN–018–0069–6720–9, Clinical Chemistry, vol. 34, No. 7, pp. 1396–1406, Jul. 1988.

James, K.R. et al., *Informix database management software in the clinical chemistry laboratory*—MED 87–10 87244856 NDN–018–0039–6461–1, Clinical Chemistry, vol. 33, No. 6, pp. 1077–8, Jun. 1987.

Xiao–Hua Zhou et al., *Comproc and Checknorm: computer programs for comparing accuracies of diagnostic tests using ROC curves in the presence of verification bias*—INS 99–03 6137827 A1999–04–8770E–024 (PHA); C1999–02–7330–308 (CCA) NDN–174–0613–7826–1, Computer Methods and Programs in Biomedicine, vol. 57, No. 3, pp. 179–86, No. 1998.

Wong, M.Y., *On the statistical analysis of bioassays*—INS 96–31 5338250 C9609–7330–127 (CCA) NDN–083–0533–8249–0, Computer Methods and Programs in Biomedicine, vol. 49, No. 3, pp. 191–7, May 1996.

Wong, M.Y., *The statistical analysis of slope ratio assays using SAS software*—INS 95–07 4877467 C9503–7330–128 (CCA) NDN–083–0487–7467–1, Computer Methods and Programs in Biomedicine, vol. 45, No. 3, pp. 233–238, Nov. 1994.

Somoza, E., *Classification of diagnostic tests*—INS 94–40 4783521 C9411–7140–019 (CCA ) NDN–083–0478–3521–4, International Journal of BioMedical Computing, vol. 37, No. 1, pp. 41–55, Sep. 1994.

Chiecchio, A. et al., *Decide: a software for computer–assisted evaluation of diagnostic test performance*—INS 93–36 4480294 C9310–7140–057 (CCA) NDN–083–0448–0294–5, Computer Methods and Programs in Biomedicine, vol. 40, No. 1, pp. 55–65, May 1993.

Zielinski, P.J. et al., *Agantg: a Microsoft Excel 5.0–visual basic routine for the analysis of dose–response data*—MED 99–05 99170776 NDN–194–0122–7863–1, Analyst, vol. 123, No. 8, pp. 1661–1668, Aug. 1998.

Iznaga, N. et al., *A personal computer–based system for parallel line analysis of bioassay data*—MED 96–0296007914 NDN–193–0097–4707–0, Computer Methods and Programs in Biomedicine, vol. 47, No. 2, pp. 167–75, Jul. 1995.

Tosetto, A. et al., *Parallel line bioassay in a coagulation laboratory. A program for personal computer use and an example application to Ristocetin Cofactor assay*—MED 92–05 92127975 NDN–192–0051–9019–7, Clin. lab. Haemat.vol. 13, No. 4, pp. 371–377, 1991.

Gaines Das, R.E. et al., *SCAN, an exploratory program for preliminary analysis of biassay and immunoassay data*—MED 86–04 86080672 NDN–018–0014–1155–2, Methods and Programs in Biomedicine, vol. 21, No. 1, pp. 25–33, Oct. 1985.

\* cited by examiner

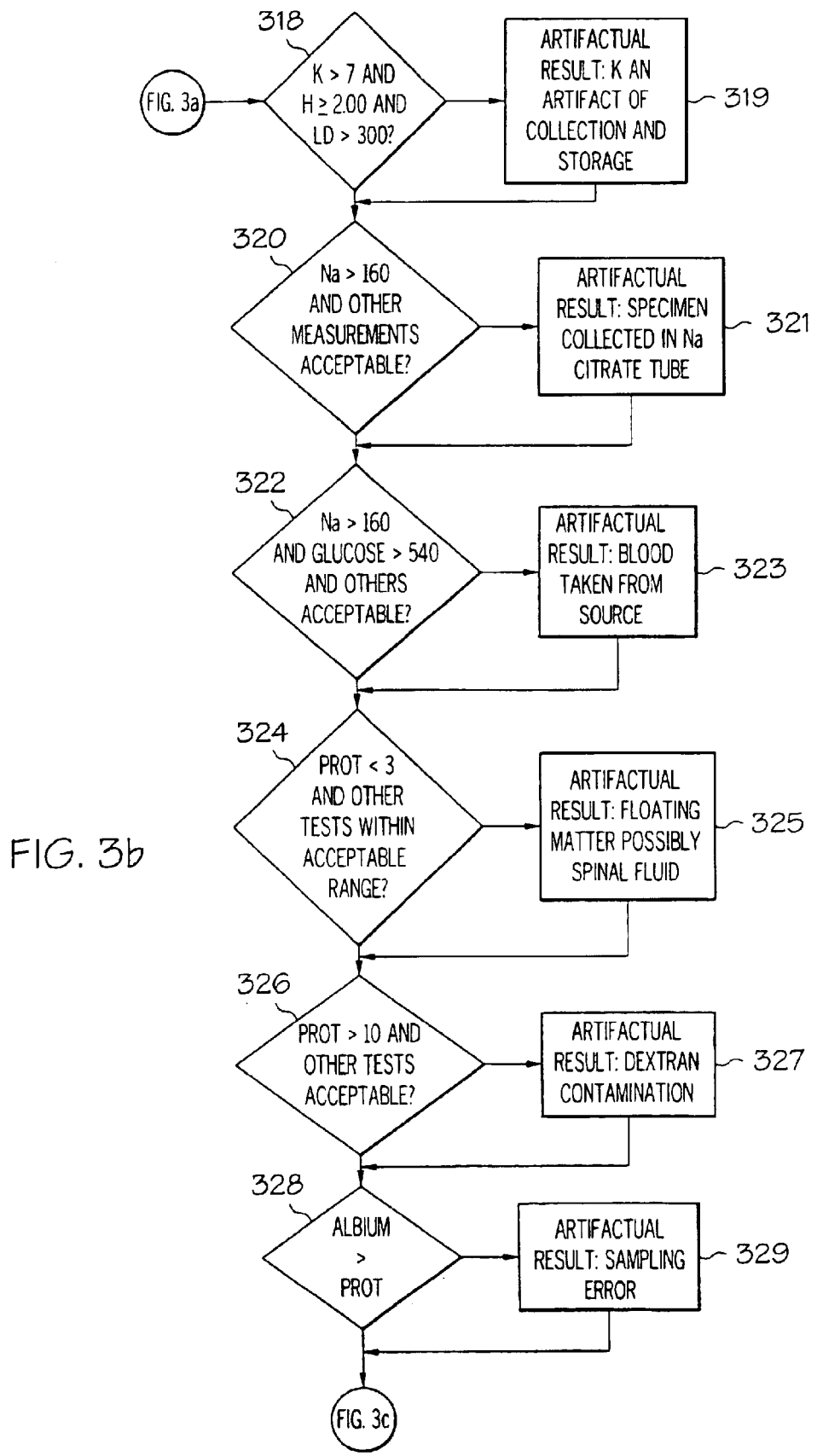

FIG. 5a

| | A | B | C | D | E | F | G |
|---|---|---|---|---|---|---|---|
| 1 | | FIELD NAME | | | | | |
| 2 | 514 | 514 | 514 | 514 | 514 | | |
| 3 | | | | | | | |
| 4 | S NO | ID | CHART NUMBER | LAST NAME | FIRST NAME | Ca | Ca_f |
| 5 | 1 | 1550270 | 5438 | SMITH | JOHN | 9.3 | R |
| 6 | 3 | 1587806 | 5439 | SMITH | JOHN | 7.9 | R |
| 7 | 4 | 1499166 | 5372 | SMITH | JOHN | 9.2 | R |
| 8 | 5 | 1403453 | 5380 | SMITH | JOHN | 8.5 | R |
| 9 | 7 | 1929063 | 5462 | SMITH | JOHN | | |

RECORDS     EXCEL DATA SHEET

FIG. 5b

FIELD NAME    RECORDS    514'    ELEMENT    FLAG   514'

| S NO | ID | CHART NUMBER | LAST NAME | FIRST NAME | Ca | Ca_f |
|---|---|---|---|---|---|---|
| 1 | 1550270 | 5438 | SMITH | JOHN | 9.3 | R |
| 3 | 1587806 | 5439 | SMITH | JOHN | 7.9 | R |
| 4 | 1499166 | 5372 | SMITH | JOHN | 9.2 | R |
| 5 | 1403453 | 5380 | SMITH | JOHN | 8.5 | R |
| 7 | 1929063 | 5462 | SMITH | JOHN | | |
| 8 | 1587809 | 5392 | SMITH | JOHN | | |

ACCESS TABLE

METHODS AND APPARATUS FOR DETECTING ARTIFACTUAL OUTPUT FROM A CHEMICAL ANALYZER

This application claims the benefit of provisional application No. 60/166,983 filed Nov. 23, 1999.

TECHNICAL FIELD

The present invention relates generally to chemical or clinical analyzers. In particular, the invention relates to a method and apparatus for automatically identifying whether data generated by a chemical analyzer contains an artifactual result, based upon expert rules, and a method and apparatus for determining possible causes of the artifactual result.

BACKGROUND OF THE INVENTION

Chemistry analyzers have been developed to automatically determine the chemical composition of a given sample. Such analyzers are also known as clinical analyzers. In the health care industry, chemistry analyzers are frequently used to analyze fluid or tissue specimens from a patient to determine whether the patient may be suffering from a disease, illness, or deficiency. A variety of tests may be performed on a particular sample, using techniques such as spectrophotometry and immunochemistry, to determine both the presence and concentration of a particular substance, in that sample. For example, various types of chromatography, spectrometry, electrophoresis, and immunochemical tests may be performed on the sample. Often, in the health care industry, such tests on blood or urine are conducted, to determine the concentrations of the various chemical constituents (i.e., analytes). For example, tests may be conducted to determine the concentrations of potassium, sodium, protein, glucose, and calcium.

Currently, automatic chemical analyzers have the capability of flagging any abnormal data taken from a tested sample with respect to a given chemical. An abnormal result may arise, either because the patient has an abnormality that reflects as a change in the activity or concentration of a particular analyte, or as a result of an error. The possible causes for the error are several and include pre-analytical errors, such as samples being collected into incorrect tubes or samples being handled incorrectly before despatch to the laboratory, or analytical errors due to incorrect machine operation, such as a bubble or clot in a flow line of the machine for example. These types of abnormal results are referred to herein as "artifactual" or "aberrant" results, and differ from abnormal results which are real and due to a physiological problem in the patient.

Abnormal results are typically flagged and reviewed before being released. One of the typical review procedures is to ascertain that the instrument is operating properly by running a quality control check on the machine. Another possible review procedure is to repeat the test, to determine if the result occurs again on the sample. However, in spite of the test being repeated and the machine passing a quality control test, the abnormal result may still remain. The technologist must decide whether the abnormal result represents a physiological abnormality in the patient, or whether the result is abnormal as a result of an artifact in the collection, handling, or analysis of the sample. The potential consequence of releasing an artifactual result as a real, physiological result, may include misdiagnosis and mistreatment, potentially resulting in harm to the patient and liability to the treating organization.

Accordingly, additional assistance in differentiating physiological from artifactual results is desired. Furthermore, it is desirable if such assistance can include the automatic identification of artifactual results, and the automatic indication of the possible causes of the artifactual result which has been identified.

SUMMARY OF THE INVENTION

It is an object of the invention to obviate the above-described problems.

It is another object of the invention to provide a method and apparatus for chemical analysis which can automatically distinguish normal results, abnormal results, and abnormal results due to an artifactual component.

Yet another object of the invention is to provide a method and apparatus for chemical analysis which can automatically detect abnormal results based on testing of a sample, and suggest causes of the abnormal result.

Another object of the invention is to provide a method and apparatus for chemical analysis which can compare various test results of an abnormal sample, and determine a potential artifactual component which caused the abnormal results.

It is another object of the invention to provide a method and apparatus for chemical analysis which can automatically identify potentially artifactual results and which utilizes commonly available input and/or output data formats which are readily modifiable.

To achieve the foregoing and other objectives, a method for analyzing clinical analysis data for potentially artifactual results is provided. The method comprises establishing a set of artifactual rules based upon experience with a clinical analyzer. Each rule identifies a potential artifactual result and associates a potential cause with the potential artifactual result. The method also comprises obtaining analytical test data results for a plurality of analytes from a sample, and determining whether any of the test data results match one or more of the established rules. If a rule is matched, the potential cause associated with the rule is indicated.

According to another aspect of the invention, an apparatus for analyzing clinical analysis data for potentially artifactual results is provided. The apparatus comprises a rule data file storing a plurality of analyte comparison concentrations which are associated with artifactual results and potential causes of the results. The apparatus also comprises an artifact determination processor which is in communication with the rule data file. The processor is configured to access a plurality of analytical test data results, compare the test data results with the analyte comparison concentrations to identify an artifactual result, and output the potential cause of the artifactual result.

Still other objects of the present invention will become apparent to those skilled in this art from the following description wherein there is shown and described preferred embodiments of this invention, including a best mode currently contemplated for carrying out the invention, simply for the purposes of illustration. As will be realized, the invention is capable of other different aspects and embodiments without departing from the scope of the invention. Accordingly, the drawings and descriptions are illustrative in nature and not restrictive in nature.

BRIEF DESCRIPTION OF THE DRAWINGS

While the specification concludes with claims particularly pointing out and distinctly claiming the invention, it is believed that the same will be better understood from the following description taken in conjunction with the accompanying drawings in which:

DETAILED DESCRIPTION OF PREFERRED EMBODIMENTS

Figure 1:
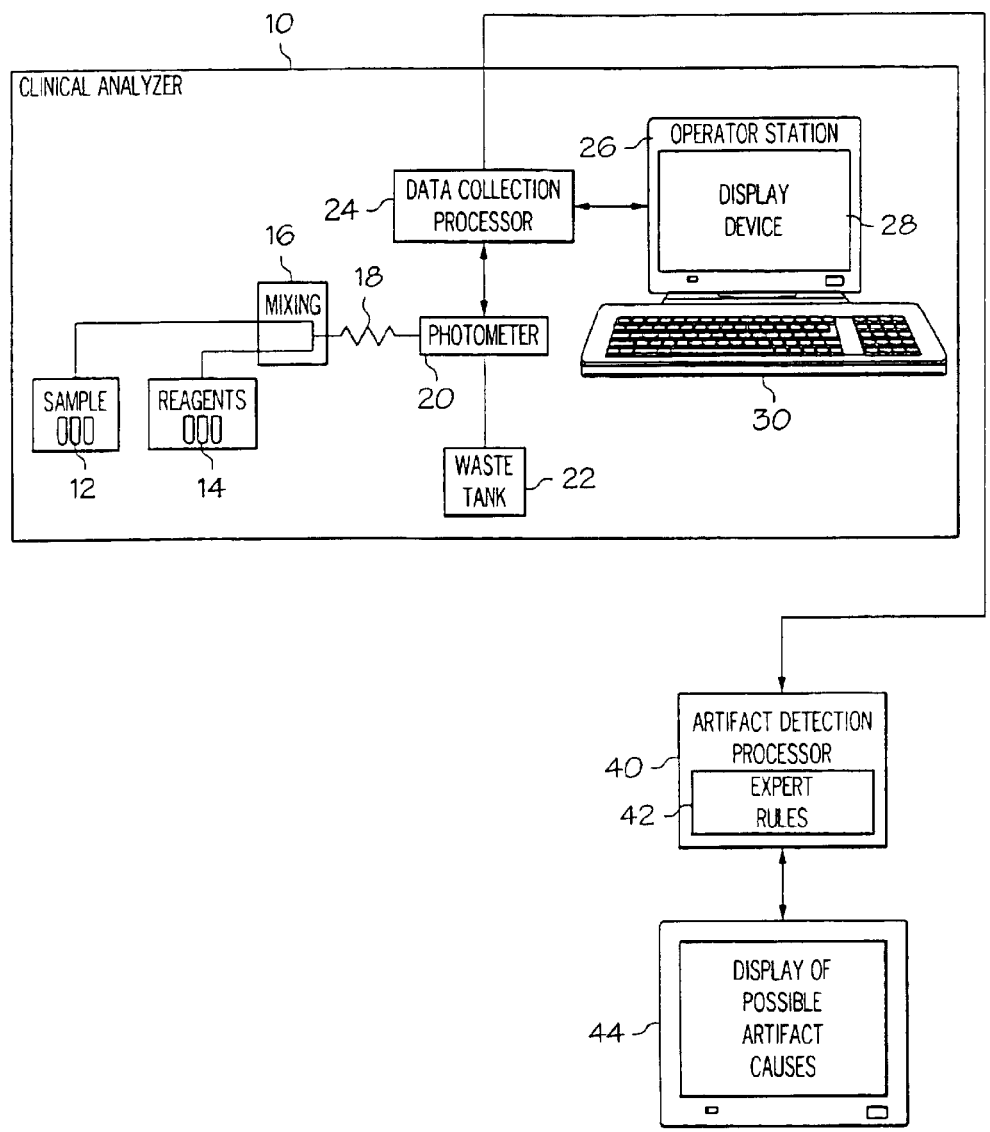
FIG. 1 is a diagram illustrating a clinical analyzer having an artifact detection processor, made in accordance with principles of the present invention.

Turning now to the drawings in detail, FIG. 1 illustrates an embodiment of a clinical analyzer, the output of which is checked for artifactual results, according to principles of the present invention. In the embodiment, the clinical analyzer 10 includes a sample container 12 which holds one or more samples of substances to be analyzed, and also a reagent container 14 which holds one or more reagents which will be mixed with the samples during the analysis. The samples could comprise human fluid, such as serum, urine, blood, or plasma, or other substances which are to be analyzed for chemical constituents. The sample container 12 could comprise tubes or cups, and a plurality of samples can be loaded by using a sample disk or tray. Likewise, a plurality of reagents can be provided for testing by using a disk or tray. Also, barcodes or other identification tags can be provided on the sample containers 12 and reagent containers 14 for identification of each substance.

Each sample is mixed with one or more reagents in the mixing container 16. If it is desired to heat the mixture to a particular temperature, a coil 18 can be utilized. Once the reagent and sample are mixed and brought to the desired temperature, a chemical reaction will proceed, and the reactive mixture is exposed to light in a photometer 20. In the photometer 20, the absorbed luminous intensity at specific wavelengths is measured, and, based on this measurement, the concentration of each chemical component is calculated by a data collection processor 24. The result of the analysis can be displayed on a display device 28 of an operator station 26. The operator station also can include an input unit 30, such as a keyboard for example, for controlling the testing process.

Each sample may be subjected to one or more tests, and each test could include one or more reagents for mixing with the sample. For example, one or more tests may be conducted on each sample to determine the concentrations of potassium, sodium, protein, glucose, and calcium in the sample. A waste tank 22 can be provided for containing the reactive mixtures after each test has been completed.

While the embodiment of FIG. 1 includes reagents and a photometer 20 for analyzing samples, it should be understood that the clinical analyzer 10 could include any suitable testing substances and devices for performing additional or alternative chemical analysis of the samples. For example, various types of chromatography, spectrometry, electrophoresis, and immunochemical tests may be performed by the clinical analyzer 10 on the sample. The data from these additional or alternative tests may also be collected by the data collection processor 24 and displayed on the display device 28.

The embodiment of FIG. 1 also includes an artifact detection processor 40 which checks the measured data obtained by the data collection processor 24 for results which may be artifactual. An artifactual or aberrant result is one which does not accurately describe the original nature of the sample, but rather includes an artificial component which has been introduced into the sample due to extraneous factors. For instance, extraneous factors involved in the collection and testing of the sample, such as human and machine interaction with the sample for instance, may cause the clinical analyzer 10 to detect a component level in the sample which is erroneous.

However, the artifact detection processor 40 is able to check the data results of a sample for such artifactual results, based upon expert rules 42 which represent empirical knowledge of the various extraneous collection and testing factors which may influence the analysis of a sample. These rules 42 are preferably derived by observing output data from the analyzer 10, determining when the data includes artifactual results, and investigating the causes of the artifactual results. Some exemplary rules which have been observed for human blood substances are described in more detail below. Preferably, according to the rules 42, the artifact detection processor 40 compares the various chemical concentrations in the sample to expected ranges for the sample. When one of the expected ranges is exceeded, an artifactual result is detected by the processor 40. In addition, the artifact detection processor 40 preferably consults the rules 42 to determine the cause of the artifactual result. For example, based upon which constituents are out of range and how far the constituents exceed the range, the rules 42 indicate a possible cause or causes of the artifactual result, based upon observations of previous sample data. The detection of the artifactual result and the possible cause or causes of the result can then be displayed by the artifact detection processor 40 on the display device 44.

As can be understood, the artifact detection processor 40, rules 42 and display device 44 can be integrated with the clinical analyzer 10, or can be embodied as a separate stand-alone unit or system. Also, the data from the data collection processor 24 can be examined by the artifact detection processor 40 on-line, during testing of samples, or off-line, after testing has been completed. The rules 42 can be implemented in a number of ways, such as by providing a set of software instructions on a computer readable medium, for example, which can be accessed by the processor 40.

Figure 2:
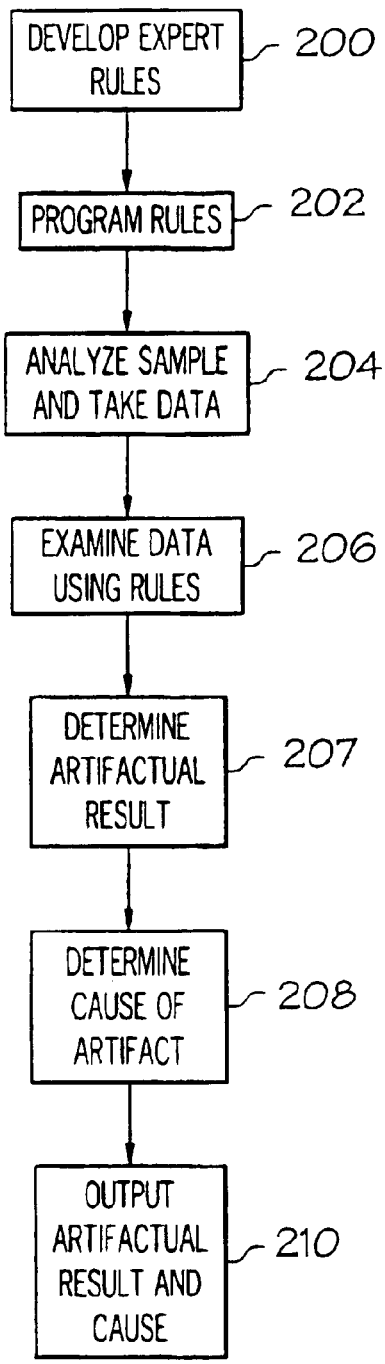
FIG. 2 is a flow diagram illustrating a method for checking data from a clinical analyzer to check for artifactual results, according to one embodiment of the present invention.

FIG. 2 is a flow diagram illustrating a method for checking data from a clinical analyzer to check for artifactual results, according to one embodiment of the present invention. According to this embodiment, a set of expert rules are developed, at step 200. The rules can be developed by observation and experience in using clinical or chemical analyzers with particular sample types. For example, data from a plurality of samples can be analyzed, and possible artifactual results flagged. Each sample having possible artifactual results can then be investigated extensively, such as by conducting additional tests on the sample or the patient from which it came, to determine whether the result is in fact artifactual, and, if so, the cause of the artifactual result. The patient's medical history can also be examined. Thus, the rules can be developed based upon individual case histories. The rules can be modified and updated based upon further examination and analysis of other samples. In this manner, the rules become more accurate and customized to the particular chemical analyzer and/or sample type.

For example, to develop the rules, a given test result from a sample can be compared to other tests on the sample or on other samples to determine when artifactual results are present. Also, results which are very unexpected or not chemically possible in light of the type of sample would also provide an indication that artifactual results might be present. To determine the cause of the artifactual result, the sample collection, preparation, and testing methods for the sample can be investigated, to determine what may have introduced the artificial component.

Once the rules have been developed to the desired degree of confidence, the rules can be programmed, such as be using a software program for example. This step is shown as block 202 of FIG. 2. For instance, each rule can comprise a comparison function to determine whether an analyte in a sample falls within a given range or ranges. Suitable software decision statements such as "If then" type statements can be utilized to make these comparisons.

Once the rules are programmed, testing can begin on samples, and data taken which indicates the analytes in the samples. This is shown at block 204 of FIG. 2. The data can then be examined using the rules to determine if the data contains one or more artifactual results. This step is shown as block 206 of FIG. 2. As an example, if one or more analytes are out of the expected range, a particular rule may be matched, and, thus, an artifactual result detected, as shown at block 207. The fact that an artifactual result has been detected may be displayed or otherwise indicated. In addition, each rule is preferably associated with one or more potential causes of the artifactual result, based upon the previous data observations and investigations. Accordingly, the potential cause of the artifactual result which is associated with the given rule can be determined, and this is shown at step 208 of FIG. 2. Once the predicted cause of the artifactual result has been selected, the artifactual result and predicted cause can be displayed or otherwise output. The cause might also be displayed with additional comments regarding suggestions for further testing on the sample to further pinpoint the cause of the result, and/or further investigation to determine whether the result is physiological.

Figure 3A:
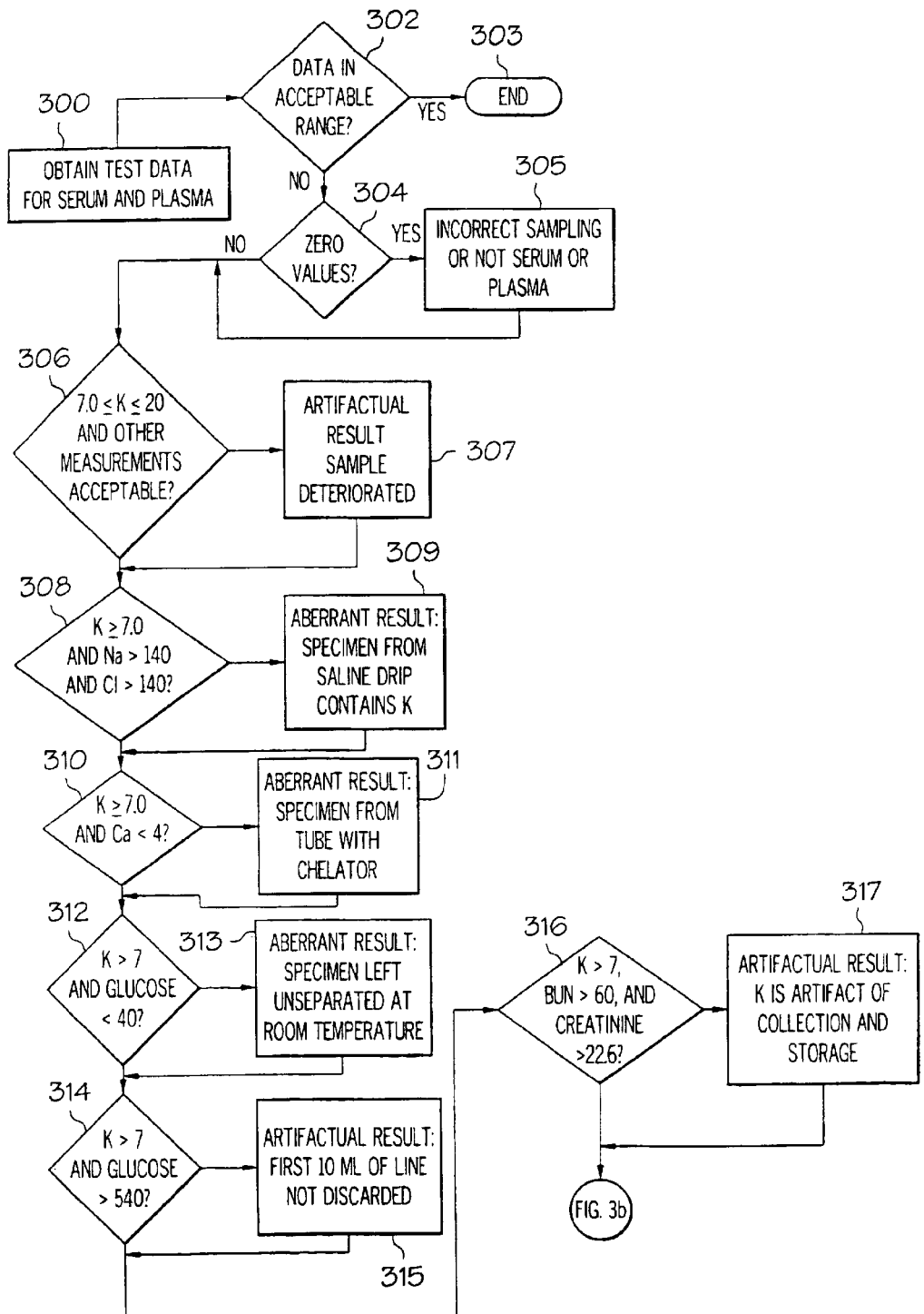
FIG. 3 is a flow diagram illustrating data checking rules to be used in testing data from a clinical analyzer for artifactual results, according to one embodiment of the present invention.
Figure 3C:
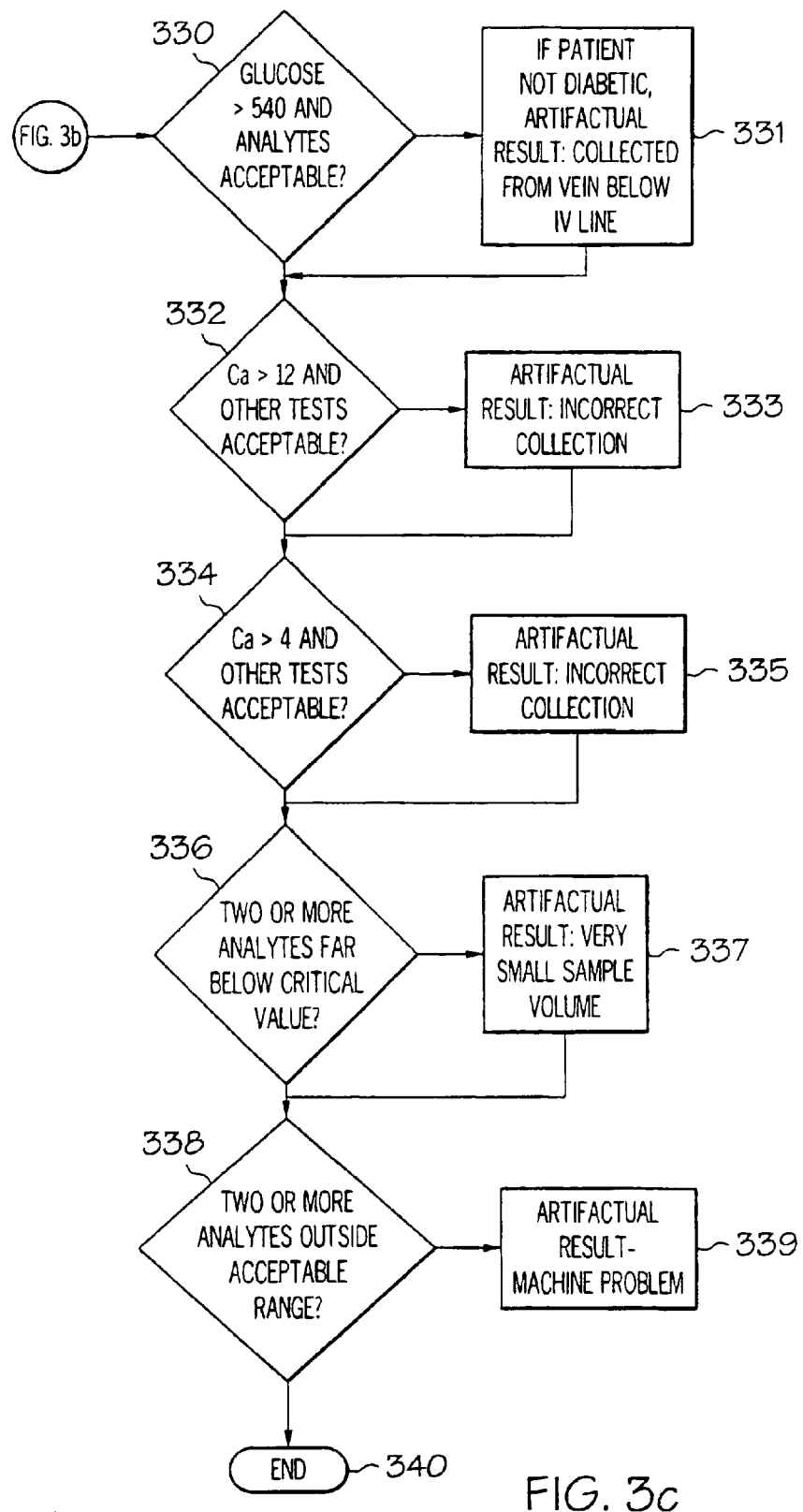

FIG. 3 is a flow diagram illustrating exemplary expert rules to be used in analyzing blood test data from a clinical analyzer for artifactual results, according to one embodiment of the present invention. According to this embodiment, the test data from analysis of a sample is obtained or read, at step 300. This data may be stored as part of a spreadsheet or other data file. Preferably, only data from serum or plasma samples are processed according to the rules in this embodiment. Data from other samples, such as urine for example, can be processed in the normal manner, or according to other rule sets. To determine, whether the sample is urine or serum/plasma, the concentration of potassium in the data can be examined. In particular, concentrations of potassium above 10 mmol/L (millimoles per liter) are most likely from urine specimens, rather than from blood-related specimens, such as serum or plasma. If the specimen is determined to be urine, the sample can be flagged as urine and, preferably, the remainder of the testing described below is skipped. Other urine-related testing can conducted on this sample.

However, if the sample is serum or plasma, at step 302, it is determined whether the data from the sample is within the acceptable range. Preferably, each constituent (i.e., analyte) in this data is compared to a list of ranges which represents what has been determined to be physiologically possible for the sample type. These values can be stored in a user-modifiable table or data file, and exemplary ranges for these values are shown below as Table 1.

TABLE 1

| Acceptable Values for Analytes | |
|---|---|
| Na | 121–159 mmol/L |
| K | 2.8–6.4 mmol/L |
| Cl | 60–140 mmol/L |
| $CO_2$ | 11–50 mmol/L |
| Ca | 1.81–2.99 mmol/L |
| Phosphate | 0.31–5.00 mmol/L |
| Urea | 1.1–90 mmol/L |
| Urate | 0.02–1.75 mmol/L |
| Creatinine | 0.04–2.00 mmol/L |
| Glucose | 2.3–29.9 mmol/L |
| Bilirubin | 2–100 mmol/L |
| Protein | 30–100 g/L |
| Albumin | 20–60 g/L |

If the data is within these acceptable ranges, the sample is classified as not being aberrant, and the process ends, at step 303. Preferably, the next sample is then analyzed.

If the data is outside of one or more of these ranges, then the process proceeds to check the data against the various rules which have been developed. In the embodiment of FIG. 3, example rules are shown in blocks 304 through 339. The first rule, at decision block 304, tests whether any of the values for the following analytes are zero: potassium, sodium, chloride, calcium, protein, albumin, LD (lactate dehydrogenase, an enzyme found in whole blood, serum, or plasma), or creatinine. If so, then the result may be artifactual. This is indicated at block 305, and the possible causes are that the sampling process was incorrect or the sample is not serum or plasma.

Rules 306 through 318 are rules involving potassium concentrations. At block 306, it is determined whether the potassium values are between 7.0 and 20 mmol per liter, and whether the other measurements are within the acceptable range of Table 1. If so, an artifactual result is detected and indicated at block 307. The predicted reason is that the sample has been allowed to deteriorate.

At block 308, it is determined if the potassium level is greater than 7 mmol/L and both sodium and chloride are higher than 140 mmol/L. If so, an artifactual result is indicated at block 309, and the most likely cause that is indicated is that the specimen was taken from a saline drip containing potassium.

Then, at block 310, it is determined if the potassium level is greater than 7 mmol/L and the calcium level is less than 4 mg/dL. If so, an artifactual result is indicated at step 311, and the most likely explanation which corresponds with this rule is that the specimen was drawn in a tube containing a chelator used to prevent blood clotting, such as EDTA (ethylenediaminetetra-acetic acid) for example. This potential cause can also be indicated at step 311. Furthermore, at this step, it may be indicated that further verification of the artifactual result may be made by performing a test for alkaline phosphatase on the specimen. A level of alkaline phosphatase less than 5 is consistent with all calcium in the sample being chelated. Ionized calcium is a necessary cofactor for the catalytic activity of this enzyme. If the activity of the alkaline phosphatase is above 5 the calcium is probably not chelated.

Step 312 tests to see if the potassium level is greater than 7 mmol/L and the glucose level is less than 40 mg/dL. If so, the result is considered artifactual, and the most probable cause is that the specimen was left unseparated at room temperature for several hours during which time the potassium leaked from the cells and the glucose was metabolized. The artifactual result and most likely cause for this rule can be displayed at step 313.

At step 314, it is determined if the potassium level is greater than 7 mmol/L and the glucose level is greater than 540 mg/dL. If so, then the result is considered artifactual, and the possible cause is that the specimen might have been taken from a central line without discarding the first 10 mL of sample. The artifact detection and possible cause for this rule are indicated, at step 315.

Step 316 determines if the potassium level is greater than 7 mmol/L, the BUN (blood urea nitrogen, also referred to as serum urea nitrogen) level is greater than 60, and the creatinine level is greater than 22.6. The high potassium level may be artifactual due to the collection and storage process. However, the high level could be physiological if the patient is in renal failure. These possibilities are output at step 317.

The next rule applies to systems which have checks for lipemia level, icteria level and hemolysis level (the so called LIH index). For these systems, if the potassium level is greater than 7 mmol/L and the H index is greater than or equal to 2.00 (but not equal to 9), and the LD level is greater than 300, then the high potassium level could be an artifact of collection and storage. This testing step is shown at step 318 in FIG. 3, and the artifactual result and possible cause are indicated at step 319.

Steps 320 through 323 represent rules which relate to sodium. At step 320, it is determined if sodium concentrations are greater than 160 mmol/L and all the other analytes are in their normal range (such as defined by an established table, such as table 1 for example). If so, then a possible artifactual result is indicated at step 321, and it is also indicated that a possible cause is that the specimen might have been collected in an Na Citrate tube. Another possible cause that may be indicated is that the sample was collected in a syringe that was used to inject Tarcil or another pharmaceutical into the normal saline infusion bag.

At step 322, it is determined if the sodium concentration is greater than 160 mmol/L the glucose level is greater than 540 mg/dL, and the other analytes are within their acceptable ranges. If this rule is satisfied, then step 323 is executed to cause an artifactual result to be indicated, the possible cause being that the blood sample was taken directly from a source such as the Vene-Section blood bag.

Rules 324 through 329 relate to rules regarding protein. Step 324 determines whether the total protein level is less than 3 g/dL, and the other tests were within their acceptable ranges. If this rule is satisfied, then an artifactual result is indicated at step 325, along with the following possible cause for that result: tiny bits of matter may be floating on the top of the specimen causing an improper sampling volume to occur. The sample may also be cerebral spinal fluid, rather than serum or plasma for which these exemplary rules were intended, and this possibility may also be indicated at step 325.

At step 326, it is determined whether the protein level is greater than 10 g/dL and the other analytes are within their acceptable ranges. If so, then the user can be informed of an artifactual result at step 327, the potential cause being dextran contamination.

Step 328 tests to determine whether the albumin level is greater than the protein level in the sample. If this is the case, then step 329 is executed, and an artifactual result is indicated. The possible cause of this result, a sampling error, is also preferably indicated at this step.

Steps 330 through 331 relate to a glucose rule. At decision block 330, it is determined if the glucose level is greater than 540 mg/dL (milligrams per deci-liter), and the other analytes are within their acceptable ranges. In this case, step 331 indicates that the patient may be diabetic, and, if not, that the result may be artifactual due to collecting the specimen at a location on a vein which is just below an intravenous (IV) line. Thus, this rule recognizes an abnormal level indicates a possible physiological problem as well as a possible artifact which may be alternatively associated with the abnormal level.

Rules 332 through 335 are exemplary rules relating to calcium concentrations. At block 332, it is determined whether the calcium level is greater than 12 mg/dL, and the other analytes are within their acceptable ranges. If this rule is met, then the abnormal level may be an artifact due to incorrect specimen collection, and this cause may be indicated at step 333.

Step 334 determines whether the calcium level is less than 4 mg/dL, and the other tests are within their acceptable ranges. If so, then the result may be artifactual due to incorrect specimen collection. To pinpoint the cause, it can be determined if the alkaline phosphatase value is near zero. If so, the specimen was probably collected with a chelating agent, such as EDTA or oxalate. The artifactual result and possible causes are indicated at step 335.

Steps 336 through 339 relate to additional rules that may be utilized in this exemplary embodiment. At step 336, it is determined whether two or more of the following analytes are far below their acceptable minimum values (such as shown in Table 1 for example): Bicarbonate, Creatinine, potassium, phosphate, glucose, protein, albumin, and urea Preferably, these analytes are checked to see if they are far below the concentrations which are physiologically possible in humans. If so, step 337 can be executed to indicate a possible artifactual result and a potential cause of this result—a very small sample volume may have been provided.

Step 338 determines whether two or more of the analytes have concentrations which are not within their acceptable ranges. When two or more such low values are found, the problem is probably an artifactual problem relating to a testing error, such as not having enough specimen placed in the reaction tube. Accordingly, step 339 is executed, and this analytical machine problem is indicated.

Once the rules have been analyzed for a given sample, then the process can be terminated, at step 340. The process can begin anew on data for another sample, if desired.

Figure 4:
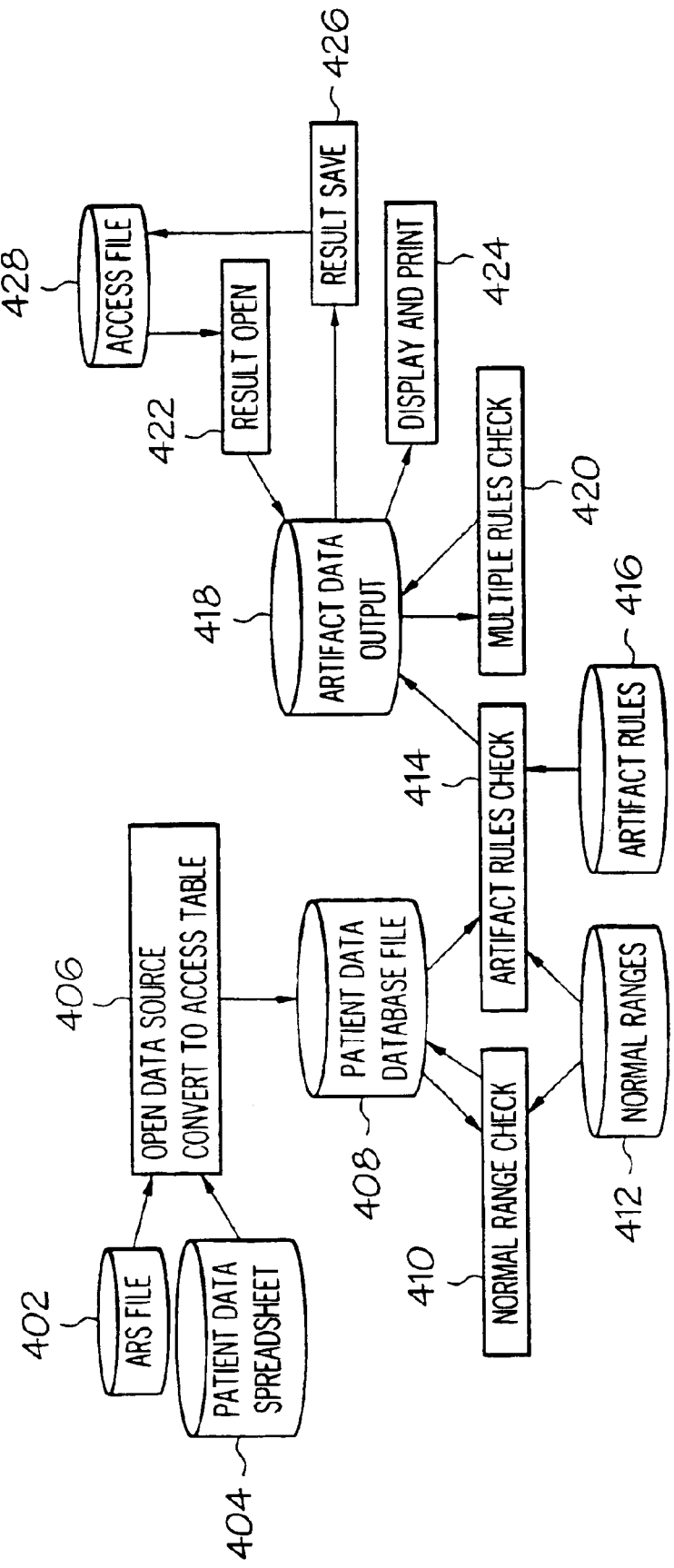
FIG. 4 is a data flow diagram illustrating the manipulation of clinical analysis data in checking for artifactual results, according to an embodiment of the present invention.

FIG. 4 is a data flow diagram illustrating the manipulation of clinical analysis data in checking for artifactual results, according to an embodiment of the present invention. This embodiment shows data collection and data processing routines which can be utilized for automatically identifying potentially artifactual results in chemical analysis data.

In this embodiment, the data from the clinical or chemical analyzer is provided in a spreadsheet format, such as a MICROSOFT EXCEL file 404. An exemplary clinical analyzer which provides data in such a format is the model 600 clinical analyzer, from Olympus Optical Clinical Instrument Division, Olympus America. The data could also be provided in an analyzer-specific format, such as an ARS file 402, which is a file format used by some Roche Diagnostics analytical equipment, such as the Hitachi Model 917.

The data conversion routine 406 then converts the input file to a database application format, such as a MICROSOFT ACCESS table 408 for example. The data in table 408 is then compared to the normal ranges for the various analytes which make up the data. These normal ranges are stored in the data file 412, which can also comprise a MICROSOFT ACCESS data file, and which is preferably alterable by the user of the system. Table 1, described above, provides an example of such ranges. The range check routine 410 checks the patient data from file 408 against the normal ranges of file 412. If the data for the analytes in the data file 408 are within the normal ranges of file 412, then no further action is taken.

However, if the patient data for a particular sample falls outside of the normal ranges, then the expert rule processing routine 414 accesses a set of rules 416, to identify whether any of the abnormal values are due to data collection and testing artifacts. The rules file 416 may also comprise a MICROSOFT ACCESS data file, and is preferably user-changeable based on additional observations and experience relating to clinical analyzers. It is preferred that each rule has a unique ID number, and that the rules are applied to the patient data file 408 according to their ID number.

For each data record in the patient data file 408 that is identified as being potentially artifactual, the rules processing routine 414 creates a data record in an artifact data output file 418. Preferably, much of the information from the identified data record is transferred to the data file 418. In addition, it is preferred that predicted cause of the artifactual result, which is provided by the rules 416, is copied to the file 418.

Once the data is created in the artifact data output file 418, a multiple artifact checking routine 420 checks to see if more than one rule has been applied to each data record. This situation can be identified by duplicate record entries having more than one artifact rule indicated. In such a situation, to save memory and reduce the amount of information needed to be reviewed, the duplicative data can be combined by the routine 420 into one record, and the multiple potential artifact causes can be indicated in one or more fields of this combined record.

After the data has been combined in the artifact data file 418, a number of output routines may be applied to the data. For example, an open routine 422 can access the data 418. The data can then be printed and/or displayed by the routine 424. Also, the output data could be saved as another file by the routine 426, such as file 428. The file 428 can also be in a common database output format, such as a MICROSOFT ACCESS data format for example.

The user can then review the data in the file 428 to assist in determining artifactual results and the possible causes of these results. In verifying artifactual results, the technician can review the medical history of the patient to see if they suffer from a particular condition. Also, the technician can compare the artifactual data to other samples which have been tested in the same time frame to try to pinpoint the cause.

FIG. 5a illustrates an example of a portion of a spreadsheet data file which could be utilized to store the patient data taken from the clinical analyzer. As shown in the figure, a number of columns are provided, including a sample number column 500 (to identify the order in which the sample was tested during the test run), a sample ID column 502 (to identify the actual sample which was tested), a chart number column 504 (to match the sample with the corresponding patient medical chart), a last name column 506 and first name column 508 (to identify the patient from which the sample was taken), an analyte level column 510 (to identify the particular analyte which was tested), and an analyte flag column 512 (to indicate when the analyte level in the preceding column was out of the normal range).

Figure 5C:
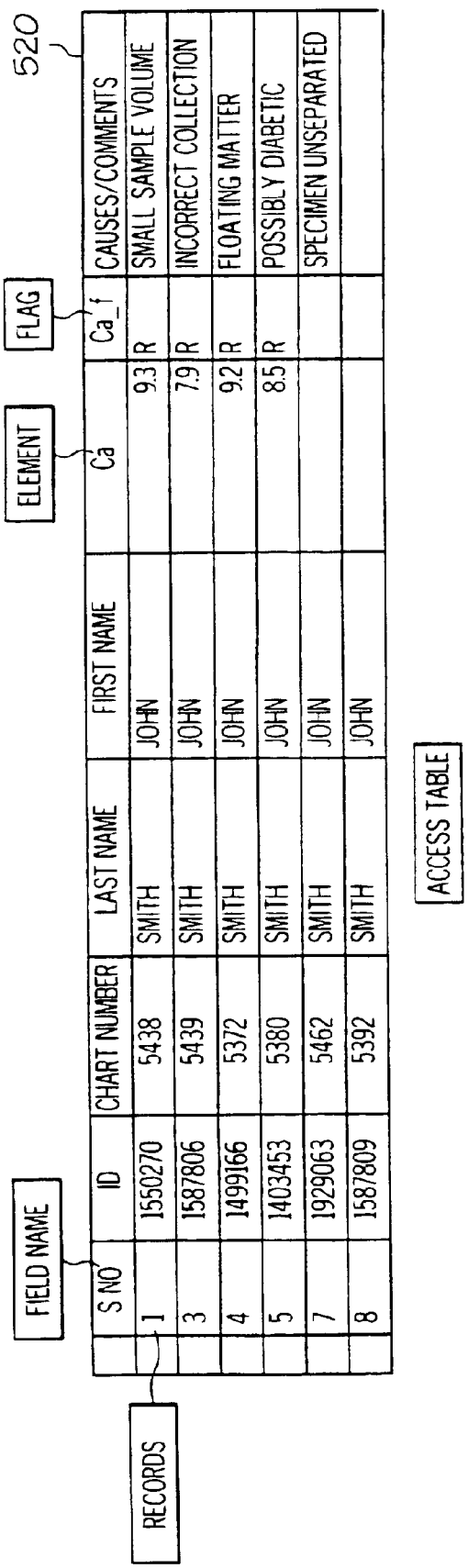
FIG. 5 shows potential data file formats which can be utilized in one or more embodiments of the present invention.

The spreadsheet data file of FIG. 5a can then be converted to a database data file, such as the exemplary portion shown in FIG. 5b. This format is similar to the spreadsheet format of FIG. 5a, except that the column titles 514 in FIG. 5a are used as field names 514' in FIG. 5b. The artifact output file which can be created using the rules described above can be similar to the format of either FIG. 5a or FIG. 5b. This file could include those sample records which were considered to be artifactual. The artifact output file could also include an additional column, such as the "Cause/Comments" column 520 shown in FIG. 5c. This column could indicate the potential cause of the artifactual result, as well as other comments which might indicate other potential physiological causes of the result, as well as methods for pinpointing the actual cause.

As can be understood, the various exemplary methods and systems described above can be implemented in a number of ways, such as by providing a set of software instructions on a computer readable medium, or by providing a programmable apparatus having executable instructions suitable for carrying out the steps stored in a RAM and/or ROM.

The foregoing descriptions of the preferred embodiments of the invention have been presented for purposes of illustration and description only. They are not intended to be exhaustive or to limit the invention to the precise forms disclosed, and modifications and variations are possible and contemplated in light of the above teachings. While a number of preferred and alternate embodiments, methods, systems, configurations, and potential applications have been described, it should be understood that many variations and alternatives could be utilized without departing from the scope of the invention. For example, components which are shown as separate can be integrated, and integrated components can be separated. Moreover, wired connections can be made wireless, and vice versa, as needed.

Thus, it should be understood that the embodiments and examples have been chosen and described in order to best illustrate the principals of the invention and its practical applications to thereby enable one of ordinary skill in the art to best utilize the invention in various embodiments and with various modifications as are suited for particular uses contemplated. Accordingly, it is intended that the scope of the invention be defined by the claims appended hereto.

What is claimed is:

1. A method for analyzing clinical analysis data for potentially artifactual results, comprising:

using a clinical analyzer to determine levels of analytes within samples taken from human patients, wherein the samples comprise specimens of matter taken from the human patients;

establishing a set of artifactual rules based upon the use of the clinical analyzer, wherein each rule identifies a potential artifactual result indicating a misleading analyte level found in the samples, and wherein each rule associates a potential artifactual result with at least one potential cause of the artifactual result, wherein the potential cause indicates why a particular analyte level indicated by the clinical analyzer is misleading, wherein at least one of the potential artifactual results corresponds with at least two chemical ranges indicating the levels of two chemicals found in the samples;

obtaining analytical test data results for a plurality of analytes corresponding to a sample taken from a human patient and tested by a clinical analyzer, wherein the sample comprises a specimen of matter taken from the human patient;

determining whether any of the test data results for the sample tested by the analyzer corresponds with one or more of the established artifactual rules; and if a corresponding artifactual rule is determined, indicating the potential cause associated with the artifactual rule, wherein the potential cause indicates an error in at least one of the collection, handling, storage, and testing of the sample which was tested by the clinical analyzer.

2. The method as recited in claim 1, further comprising:

determining whether the test data results for the plurality of analytes meets the acceptable ranges for the analytes.

3. The method as recited in claim 2, wherein the acceptable ranges are stored in a user-modifiable data file.

4. The method as recited in claim 1, wherein the rules are stored in a user-modifiable data file.

5. The method as recited in claim 1, wherein the potential cause is indicated by storing the potential cause in an output data file.

6. The method as recited in claim 1, wherein the potential cause is indicated by displaying the potential cause.

7. The method as recited in claim 1, wherein the analytical test data results are provided in a spreadsheet format.

8. The method as recited in claim 7, wherein the potential cause is indicated by storing the potential cause in an output data file which is in a database application format.

9. The method as recited in claim 1, wherein the test data results comprise data representing the levels of at least two of the following chemicals in the sample: potassium, sodium, calcium, protein, albumin, lactate dehydrogenase, and creatinine.

10. The method as recited in claim 1, wherein the determining operation is conducted by:

comparing first test data results with an expected range for the first test data results, wherein the first test data results represent at least one of potassium and protein; and comparing second test data results with an expected range for the second test data results, wherein the second test data results represents at least one of potassium, sodium, glucose, calcium, and albumin, and wherein at least one rule is associated with the first and second test data results exceeding their corresponding ranges.

11. An apparatus for analyzing clinical analysis data for potentially artifactual results, comprising:

rule data storing a plurality of analyte comparison concentrations which are associated with artifactual results and determined from analyzing samples using a clinical analyzer, wherein the rule data stores potential causes of the artifactual results; and an artifact determination processor in communication with the rule data and configured to access a plurality of analytical test data results including analyte concentration levels obtained from testing samples of matter using a clinical analyzer, wherein the processor is further configured to compare the analyte concentration levels from the clinical analyzer with the analyte comparison concentrations in the rule data to identify an artifactual result, and to output the potential cause of the artifactual result, wherein the potential cause indicates an error in at least one of the collection, handling, storage, and testing of a sample which was tested by the clinical analyzer; and a clinical analyzer configured to provide the analytical test data results, and an input data file configured to store the analytical test data results; and an output data file configured to store the potential cause of identified artifactual results.

12. The apparatus as recited in claim 11, wherein the input data file is in a spreadsheet format and the output data file is in a database format.

* * * * *